United States Patent [19]

Payne

[11] 4,330,555
[45] * May 18, 1982

[54] INDANYLOXAMIC DERIVATIVES, THEIR PREPARATION AND PHARMACEUTICAL COMPOSITIONS CONTAINING THEM

[75] Inventor: Trevor G. Payne, Arlesheim, Switzerland

[73] Assignee: Sandoz Ltd., Basel, Switzerland

[*] Notice: The portion of the term of this patent subsequent to Apr. 10, 1996, has been disclaimed.

[21] Appl. No.: 104,409

[22] Filed: Dec. 17, 1979

[30] Foreign Application Priority Data

Dec. 22, 1978 [CH] Switzerland ............... 13115/78

[51] Int. Cl.³ ............... A61K 31/195; A61K 31/215; C07C 101/447
[52] U.S. Cl. ............... 424/309; 424/319; 560/43; 562/457
[58] Field of Search ............... 562/433, , 455, 457; 560/43; 424/309, 319

[56] References Cited
U.S. PATENT DOCUMENTS 4,057,556  11/1977  Bagli et al. ............... 424/319
4,069,343   1/1978  Sellstedt et al. ............ 424/319
4,119,783  10/1978  Hall et al. ............... 562/433
4,148,916   4/1979  Payne ................... 424/309

*Primary Examiner*—Natalie Trousof
*Assistant Examiner*—L. Hendriksen
*Attorney, Agent, or Firm*—Gerald D. Sharkin; Timothy G. Rothwell

[57] ABSTRACT

The invention provides compounds of formula I,

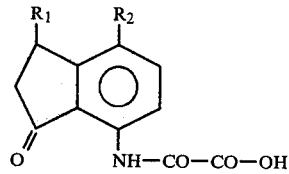

wherein
 $R_1$ is hydrogen or alkyl($C_{1-10}$), and
 $R_2$ is alkyl($C_{1-10}$), and physiologically acceptable and hydrolysable esters thereof, useful as anti-allergic agents.

9 Claims, No Drawings

INDANYLOXAMIC DERIVATIVES, THEIR PREPARATION AND PHARMACEUTICAL COMPOSITIONS CONTAINING THEM

This invention relates to indanyloxamic derivatives, their preparation and pharmaceutical compositions containing them.

The present invention provides compounds of formula I

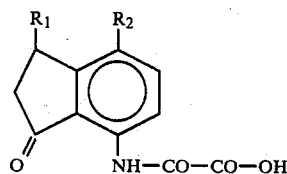

wherein
$R_1$ is hydrogen or alkyl($C_{1-10}$), and
$R_2$ is alkyl ($C_{1-10}$),
and physiologically acceptable and hydrolysable esters thereof.

Preferably $R_1$ and/or $R_2$ when alkyl is of 1 to 5 carbon atoms. A physiologically acceptable and hydrolysable ester is an ester which splits under physiological conditions to the corresponding acid. Such esters include alkyl esters, e.g. alkyl($C_{1-4}$) esters, aryl esters, e.g. those wherein aryl is phenyl, optionally monosubstituted by chlorine, bromine, alkyl($C_{1-4}$) or alkoxy($C_{1-4}$), and cycloalkyl esters. The alkyl($C_{1-4}$) esters are preferred.

The present invention provides a process for the production of a compound of formula I, as defined above, or a physiologically acceptable and hydrolysable ester thereof, which comprises (a) to obtain a physiologically acceptable and hydrolysable ester of a compound of formula I, acylating a compound of formula II,

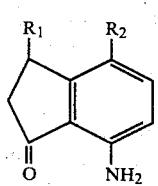

wherein $R_1$ and $R_2$ are as defined above, with an appropriate acylating agent, or (b) to obtain a compound of formula I, hydrolysing a corresponding ester of a compound of formula I.

The above acylation process may be effected in conventional manner for the acylation of an arylamine to obtain an aryloxamic acid ester, e.g. with an appropriate oxalic acid mono-ester mono-halide, or acid di-ester, which may, for example, be of formula:

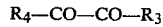

R$_4$—CO—CO—R$_3$      III wherein
$R_3$ is alkoxy($C_{1-4}$), phenoxy or phenoxy monosubstituted by chlorine, bromine or alkyl($C_{1-4}$) or alkoxy($C_{1-4}$), and
$R_4$ is chlorine, bromine, alkoxy($C_{1-4}$), phenoxy or phenoxy monosubstituted by chlorine, bromine, alkyl($C_{1-4}$) or alkoxy($C_{1-4}$).

Preferably $R_3$ is the same as $R_4$ or else $R_4$ is chlorine or bromine.

Suitable reaction temperatures may be from about $-5°$ C. to about 200° C. An inert solvent may be present or alternatively an excess of a compound of formula III. If desired, a basic catalyst such as triethylamine or pyridine may be present.

The hydrolysis reaction may be effected in conventional manner for the hydrolysis of analogous oxamic acid esters. Preferred esters include the alkyl ($C_{1-4}$) esters and the optionally substituted phenyl esters mentioned above. Preferably, the reaction is effected in appropriate basic conditions, e.g. in the presence of dilute alkali or tertiary amine. Suitable reaction temperatures are from about 0° C. to the reflux temperature. If desired, a water-miscible solvent, such as alcohol, dimethylsulphoxide or dimethoxyethane, may be present.

The free acid forms of a compound of formula I may be converted into anionic salt forms in conventional manner and vice versa. Suitable anionic salt forms include the sodium, potassium, calcium or magnesium salts, or may be derived from organic amines.

The starting material of formula II may be obtained as follows:

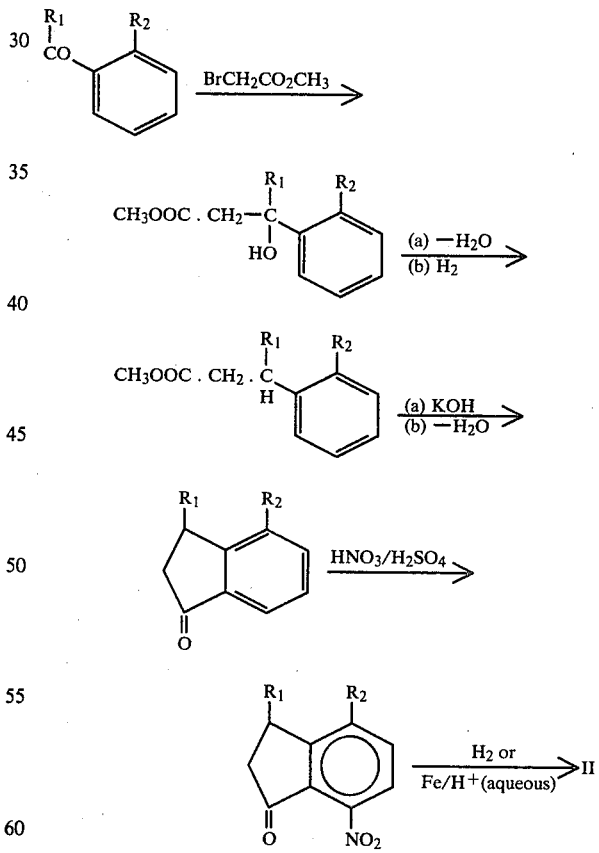

Insofar as the production of any particular starting material is not particularly described, this may be made in conventional manner for analogous compounds or by processes described herein.

In the following Examples all temperatures are in degrees Centigrade and are uncorrected.

EXAMPLE 1

N-(7-Methyl-3-oxo-1-propyl-4-indanyl)oxamic acid ethyl ester

A solution of 7.2 g of 7-methyl-3-oxo-1-propyl-4-indanylamine in 34 ml oxalic acid diethyl ester is boiled under reflux for 2 hours and then cooled to room temperature. The reaction mixture is then heated at 90°–100° at 11 mm Hg to remove the excess oxalic acid diethyl ester. The residue is chromatographed on 200 g silica gel to afford the pure title compound which is recrystallised from ether. M.pt. 84°–86°.

The starting material is obtained as follows:

(a) A solution of 50 ml 2-methylbutyrophenone and 112 ml bromo-acetic acid methyl ester in 92 ml benzene is added dropwise to a boiling suspension of 150 g zinc turnings in 480 ml benzene. The mixture is boiled with stirring for a further 3 hours, cooled to room temperature and then filtered, e.g. through a filtering aid such as Hyflo (Registered Trade Mark). The filtrate is concentrated, taken up in $CHCl_3$, washed with water, dried over sodium sulphate and the solution concentrated. The oily crude 3-hydroxy-3-(o-tolyl)-hexanoic acid methyl ester is filtered in $CHCl_3$ through silica gel and used in the next stage as such.

(b) A solution of 58.9 g of 3-hydroxy-3-(o-tolyl)-hexanoic acid methyl ester, 1.1 g p-toluene sulphonic acid and 2.5 ml concentrated $H_2SO_4$ in 400 ml toluene is boiled in a water separator under reflux. The resultant reaction solution is concentrated, taken up in $CHCl_3$, washed with $NaHCO_3$ solution, $H_2O$ and then NaCl solution and then concentrated. The crude product in $CHCl_3$ is filtered through silica gel and the filtrate concentrated. The product containing 3-(o-tolyl)-hex-2- and/or 3-enoic acid methyl ester is taken up in 400 ml methanol and hydrogenated in the presence of 2.1 g 10% (by weight) Palladium on charcoal at 20° and at 1.1 atmospheres to yield 3-o-tolyl-hexanoic acid methyl ester, which is further worked up as such.

(c) 32 g of 3-o-tolyl-hexanoic acid methyl ester obtained from step (b) in 200 ml methanol are boiled under reflux with 9.8 g KOH in 20 ml $H_2O$ for 2 hours. Isolation of the acid product yields 3-o-tolyl-hexanoic acid as an oil.

(d) 29 g of 3-o-tolyl-hexanoic acid, obtained from step (c), are stirred in 145 g polyphosphoric acid at 100° and then stirred for 2 hours at 100°. The mixture is treated with ice, diluted with water and extracted with chloroform. The extracts are washed with water, dried over $Na_2SO_4$ and concentrated. The residue is distilled at 180°/10 mm to give oily 4-methyl-3-propyl-1-indanone.

(e) A solution of 5.9 g of 4-methyl-3-propyl-1-indanone, obtained from step (d) in 23 ml concentrated sulphuric acid is prepared and to this is added dropwise a solution of 3.8 g potassium nitrate in 35.4 ml concentrated sulphuric acid at $-5°$ C. The mixture is stirred for $1\frac{1}{2}$ hours at 0° C., and is then treated with ice, diluted with water and extracted with methylene chloride. The resultant mixture of 6-nitro- and 7-nitro-4-methyl-3-propyl-1-indanones is dissolved in methanol and hydrogenated in the presence of 0.5 g (10% by weight) Palladium on charcoal. The mixture is filtered, concentrated and chromatographed on silicagel to afford pure 7-methyl-3-oxo-1-propyl-4-indanylamine.

EXAMPLE 2

N-(1-Ethyl-7-methyl-3-oxo-4-indanyl)oxamic acid ethyl ester

The title compound is prepared in analogous manner to Example 1 (M.pt. 120°–123°) and the starting material is produced in analogous manner to Example 1, steps (a) to (e).

EXAMPLE 3

N-(7-Methyl-3-oxo-1-propyl-4-indanyl)oxamic acid

A solution of 1.6 g N-(7-methyl-3-oxo-1-propyl-4-indanyl)oxamic acid ethyl ester in 100 ml methanol is heated at reflux with 5.28 ml of 1 M aqueous NaOH for 30 minutes. The solution is concentrated, diluted with water, filtered through a filtering aid such as Hyflo (Registered Trade Mark), and made acid with 2 N HCL. The title compound is filtered off and dried. M.Pt. 157°–158°.

EXAMPLE 4

N-(1-Ethyl-7-methyl-3-oxo-4-indanyl)oxamic acid

Hydrolysis of N-(1-ethyl-7-methyl-3-oxo-4-indanyl)-oxamic acid ethyl ester in analogous manner to Example 3 yields the title compound, m.p. 176°–177°.

EXAMPLE 5

N-(7-n-decyl-3-oxo-4-indanyl)oxamic phenyl ester may be produced in analogous manner to Example 1 and hydrolysed in analogous manner to Example 3.

The compounds of formula I, and physiologically acceptable and hydrolysable esters thereof possess pharmacological activity. In particular, the compounds possess disodium chromoglycate (DSCG)-like activity, and are therefore useful in the treatment and prophylaxis of allergic conditions, such as allergic asthma, exercise-induced asthma and allergic gastro-intestinal disorders, as indicated in the passive cutaneous anaphylaxis (PCA) test in the rat, according to the principles of U. Martin and D. Roemer [Arzneimittel Forschung/Drug Research 28(1) 5, 770–782 (1978)].

In the test employed, the rats receive 0.1 to 3.2 mg/kg i.v., or 1 to 32 mg/kg p.o., of the compounds, one minute, or 7.5 to 15 minutes, (respectively) before histamine injection. The histamine-release inhibitor activity can be confirmed by inhibition of histamine release in the passive peritoneal anaphylaxis test in the rat, carried out according to the description in the above publication on administration from about 0.1 to about 3.2 mg/kg i.v. with the compounds.

It is to be appreciated that activity of the physiologically acceptable and hydrolysable esters of compounds of formula I may only be observed after their hydrolysis to compounds of formula I.

For the above-mentioned uses, the dosage will, of course, vary depending on the compound employed, mode of administration and therapy desired. However, in general, satisfactory results are obtained when administered at a daily dosage of from about 0.1 to about 100 mg/kg of animal body weight, conveniently given in divided doses 2 to 4 times a day or in sustained release form. For the larger mammal, the total daily dosage is in the range of from about 0.5 to about 100 mg, and dosage forms suitable for oral administration comprise from about 0.1 to about 50 mg of the compounds admixed with a solid or liquid pharmaceutical carrier or diluent.

The compounds of formula I may be administered in pharmaceutically acceptable anionic salt forms. Such salt forms have the same order of activity as the free forms. The present invention provides a pharmaceutical composition comprising a compound of formula I or a physiologically acceptable and hydrolysable ester thereof, in association with a pharmaceutical diluent or carrier. Such compounds may be formulated in conventional manner to be, for example, a tablet or solution.

I claim:

1. A compound of formula (I)

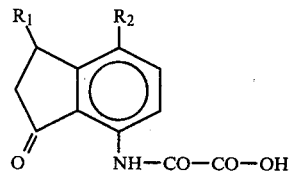

wherein $R_1$ is hydrogen or alkyl ($C_{1-10}$), and
$R_2$ is alkyl ($C_{1-10}$), or a pharmaceutically acceptable salt thereof, or a physiologically acceptable and hydrolysable ester thereof selected from the group consisting of the alkyl esters wherein alkyl has 1 to 4 carbon atoms, phenyl esters and phenyl esters monosubstituted by chlorine, bromine, alkyl having 1 to 4 carbon atoms or alkoxy having 1 to 4 carbon atoms.

2. A compound of claim 1, wherein the ester is an alkyl($C_{1-4}$) ester.

3. A compound of formula I, defined in claim 1, or a salt thereof.

4. A compound of claim 1, which is N-(7-methyl-3-oxo-1-propyl-4-indanyl)oxamic acid ethyl ester.

5. A compound of claim 1, which is N-(1-ethyl-7-methyl-3-oxo-4-indanyl)oxamic acid ethyl ester.

6. A compound of claim 1, which is N-(7-methyl-3-oxo-1-propyl-4-indanyl)oxamic acid or a salt thereof.

7. A compound of claim 1, which is N-(1-ethyl-7-methyl-3-oxo-4-indanyl)oxamic acid or a salt thereof.

8. A pharmaceutical composition for use in treating or effecting prophylaxis of allergic conditions comprising an effective amount of a compound of claim 1 or a physiologically acceptable and hydrolysable ester thereof, in association with a pharmaceutical diluent or carrier.

9. A method of treating or effecting prophylaxis of allergic conditions in animals which comprises administering a compound of claim 1 to an animal in need of such treatment.

* * * * *